US012718356B2

(12) United States Patent
Natarajan et al.

(10) Patent No.: US 12,718,356 B2
(45) Date of Patent: Aug. 25, 2026

(54) SYNTHETIC GENERATION OF CLINICAL SKIN IMAGES IN PATHOLOGY

(71) Applicant: Google LLC, Mountain View, CA (US)

(72) Inventors: Vivek Natarajan, Mountain View, CA (US); Yuan Liu, Mountain View, CA (US); David Coz, Mountain View, CA (US); Amirata Ghorbani, Mountain View, CA (US)

(73) Assignee: Google LLC, Mountain View, CA (US)

( * ) Notice: Subject to any disclaimer, the term of this patent is extended or adjusted under 35 U.S.C. 154(b) by 1107 days.

(21) Appl. No.: 17/768,419

(22) PCT Filed: Oct. 13, 2020

(86) PCT No.: PCT/US2020/055346

§ 371 (c)(1),
(2) Date: Apr. 12, 2022

(87) PCT Pub. No.: WO2021/086594

PCT Pub. Date: May 6, 2021

(65) Prior Publication Data

US 2024/0119586 A1 Apr. 11, 2024

Related U.S. Application Data

(60) Provisional application No. 62/926,783, filed on Oct. 28, 2019.

(51) Int. Cl.
*G06T 7/00* (2017.01)
*G06T 11/10* (2026.01)
(Continued)

(52) U.S. Cl.
CPC ............ *G06T 7/0012* (2013.01); *G06T 11/10* (2026.01); *G16H 10/60* (2018.01); *G16H 50/70* (2018.01);
(Continued)

(58) Field of Classification Search
None
See application file for complete search history.

(56) References Cited

U.S. PATENT DOCUMENTS

2004/0264749 A1* 12/2004 Skladnev ............ A61B 5/0059 382/128
2014/0313303 A1* 10/2014 Davis ...................... A61B 5/68 348/77
(Continued)

FOREIGN PATENT DOCUMENTS

CN 108198620 6/2018
CN 108921179 A * 11/2018 .......... G06F 18/2411
(Continued)

OTHER PUBLICATIONS

Isola et al., "Image-to-Image Translation with Conditional Adversarial Networks", Arxiv.org, Cornell University Library, 201 Olin Library Cornell University Ithaca, NY 14853, Nov. 21, 2016, pages.
(Continued)

*Primary Examiner* — Mohammed Rachedine
(74) *Attorney, Agent, or Firm* — McDonnell Boehnen Hulbert & Berghoff LLP

(57) ABSTRACT

We disclose the generation and training of Generative Adversarial Networks (GAN) to synthesize clinical images with skin conditions. Synthetic images for a pre-specified skin condition are generated, while being able to vary its size, location and the underlying skin color. We demonstrate that the generated images are of high fidelity using objective GAN evaluation metrics. The synthetic images are not only visually similar to real images, but also embody the respective skin conditions. Additionally, synthetic skin images can be used as a data augmentation technique for training a skin condition classifier, and improve the ability of the classifier to detect rare but malignant conditions.

17 Claims, 8 Drawing Sheets

(51) Int. Cl.
*G16H 10/60* (2018.01)
*G16H 50/70* (2018.01)

(52) U.S. Cl.
CPC ............... *G06T 2207/20081* (2013.01); *G06T 2207/20084* (2013.01); *G06T 2207/20104* (2013.01); *G06T 2207/30088* (2013.01); *G06T 2207/30096* (2013.01)

(56) References Cited

U.S. PATENT DOCUMENTS

| | | | | |
|---|---|---|---|---|
| 2017/0287134 | A1 | 10/2017 | Abedini et al. | |
| 2018/0061046 | A1* | 3/2018 | Bozorgtabar | G06T 7/0012 |
| 2018/0130203 | A1* | 5/2018 | Abedini | G06T 7/0012 |

FOREIGN PATENT DOCUMENTS

| | | | | | |
|---|---|---|---|---|---|
| CN | 108961272 | | | 12/2018 | |
| CN | 108961272 | A | * | 12/2018 | G06T 7/11 |
| CN | 109785399 | | | 5/2019 | |
| CN | 107563997 | B | * | 6/2020 | |
| WO | WO-2014172671 | A1 | * | 10/2014 | G16H 70/60 |

OTHER PUBLICATIONS

International Search Report and Written Opinion for International Application No. PCT/US2020/055346 dated Jan. 19, 2021, 54 pages.

* cited by examiner

Real images - left column
Synthetic images - right column

800
Preprocess heterogeneous dataset
802
Training set
804
Add synthetic images from trained GAN to training set
806
Train classifier from augmented training set
808

906
Semantic map
1
image
Semantic map
N
image
Semantic map
CPU
[ Trained GAN ]
904
902
Synthetic image
910
900

SYNTHETIC GENERATION OF CLINICAL SKIN IMAGES IN PATHOLOGY

CROSS-REFERENCE TO RELATED APPLICATIONS

This application is a US national phase application of International Patent Application No. PCT/US2020/055346 filed on Oct. 13, 2020, which claims priority to U.S. Provisional Patent Application Ser. No. 62/926,783, filed Oct. 28, 2019, each of which is incorporated herein by reference in its entirety.

BACKGROUND

This disclosure relates to a method and machine learning architecture for synthetic generation of clinical images of skin with various pathological conditions, such as melanoma, squamous cell carcinoma, skin tag, etc. The methodology allows for the ability to generate synthetic images and in the process modify the size of the pathology, the type of pathology and/or the underlying skin color.

The combination of large scale data and advances in computing has catalyzed the success of supervised deep learning in many domains including computer vision, natural language processing and speech recognition. Over the last few years, several efforts have been made to apply supervised deep learning to various medical imaging tasks, such as disease classification, detection of suspicious malignancy and organ segmentation on different imaging modalities including ophthalmology, pathology, radiology, cardiology, and dermatology.

Despite this progress, developing effective deep learning models for these tasks remains non-trivial mainly due to the data hungry nature of such algorithms. Most previous efforts that report expert-level performance required large amounts of expert annotated data (multiple thousands and sometimes even millions of training examples). However, the cost of obtaining expert-level annotations in medical imaging is often prohibitive. Moreover, it is nearly impossible to collect diverse datasets that are unbiased and balanced. Most of the data used in medical imaging and other healthcare applications come from medical sites which may disproportionately serve certain specific patient demographics and be under-represented in other patient demographics. Such datasets also tend to have very few examples of rare conditions because they naturally occur sparingly in the real world. Models trained on such biased and unbalanced datasets tend to perform poorly on test cases drawn from under-represented populations or on rare conditions.

There has been remarkable progress in generative machine learning models in recent years. Generative Adversarial Networks (GANs) in particular, have emerged as the de facto standard for generating diverse and high quality sample images. These networks are described in detail in the following publication: I. Goodfellow, et al., *Generative adversarial nets*, Advances in Neural Information Processing Systems, vol. 263 pp. 2672-2680 (2014). The entire content of the Goodfellow et al. article is incorporated by reference herein. Such networks have been effectively used in many applications, including super-resolution, text-to-image generation, and in the medical domain, generating medical records, liver lesion images, bone lesion images and anomaly detection.

In dermatology, prior efforts on applying generative models to synthesize images have focused on datasets of dermoscopic images. Dermoscopic images are acquired using specialized equipment (dermatoscopes) in order to have a clean, centered, and zoomed-in image of the skin condition under normalized lighting. However, access to dermatoscopes is limited: they are often only available in dermatology clinics and are used to examine certain lesion conditions. On the other hand, clinical images are taken by consumer grade cameras (point-and-shoot cameras or smartphones), and are thus much more accessible to general users. Such images can be used either in a tele-dermatology setting, where patients or general practitioners can send such photographs to dermatologists for diagnosis, or to directly leverage AI based tools for informal patient self-diagnosis. However, acquisition of such images is not part of the standard clinical workflow, leading to a data void to develop well-performing skin disease classification models. Last but not least, unlike dermoscopic images, clinical images of skin conditions have diverse appearances in terms of scale, perspective, zoom effects, lighting, blur and other imaging artifacts. In addition, the presence of hair, various skin colors, and body parts, age-induced artifacts (e.g., wrinkles), and background also contribute to the diversity of clinical data. Such diversity makes it challenging for generative models to learn the underlying image representation.

To the best of our knowledge, no prior work has attempted to synthesize clinical images (i.e., images obtained with consumer grade cameras) with skin pathology.

SUMMARY

In this document, we provide a system and method for generating synthetic images of skin with pathology taken by consumer grade cameras. We formulate the problem as an image to image translation framework and use an adapted version of the existing GAN-based image translation architectures. Specifically, our model learns to translate a semantic map with a pre-specified skin condition, its size and location, and the underlying skin color, to a realistic image that preserves the pre-specified traits. In this way, images of rare skin conditions in minority demographics can be generated to diversify existing datasets for the downstream skin condition classification task. We demonstrate via both GAN evaluation metrics and qualitative tests that the generated synthetic images are of high fidelity and represent the respective skin condition. When we use the synthetic images as additional data to train a skin condition classifier, we observe that the model improves on rare malignant classes while being comparable to the baseline model overall.

Thus, in one aspect, synthetically generated images can be used as training images which supplement real clinical images as input for training a skin condition classifier, e.g., deep convolutional neural network, for example to remove bias in the training set and/or provide more examples of rare conditions in a variety of different types of skin colors. Additionally, the synthetic skin images can be provided or made available to clinicians or the public as examples of skin pathologies for various skin colors and facilitate education, or informal self-diagnosis. For example, databases for image search engines may have large collections of images of a particular pathology (e.g., Lyme disease) in people having white skin, but lack images of the pathology in people with dark skin. The inventors provide a way to generate synthetic skin images to make such image databases much more representative, remove bias in the databases, and provide examples of rare conditions across the entire spectrum of human skin color.

In one aspect, the disclosure is directed to a method of synthetic generation of clinical skin images with pathology.

The method makes use of a heterogeneous dataset in the form of a multitude of ground truth annotated clinical skin images presenting a variety of pathologies and obtained from a multitude of patients with varying degrees of skin color. An example is given of a dataset in the form of 49,920 images generated by a teledermatology service. The images were annotated with ground truth by board certified dermatologists to differentiate among 26 common skin conditions and an additional 'other' category. The dataset of skin images was generated by consumer grade cameras, e.g., cameras embodied in smart phones, tablets or off-the shelf consumer cameras, in contrast to datasets of images generated by special purpose equipment (dermascope images).

The images in the dataset include extraneous features including hair, clothing, etc. and the background is unique to each individual and non-uniform across the dataset. To improve the signal to noise ratio, a preprocessing step is performed on the dataset: creating one or more region of interest (ROI) bounding boxes for each image such that the pathology present in the clinical skin images is prominent within such bounding boxes, thereby creating a more uniform version of the data set. These images within ROI bounding boxes are referred to as "cropped images" in this document. This more uniform version is referred to as the "training set" below.

The methodology further includes a step of, for each image in the training set created as described above, generating a corresponding semantic map m that encodes the skin color, pathology, size and location of the pathology within the image (ROI), thereby generating input pairs $\{x_i; m_i\}$ where $x_i$ is an image in the training set, and i=1 . . . N, where N is the number of cropped images in the training set;

The methodology then includes a step of training a generative adversarial network (GAN) with the input pairs $\{x_i; m_i\}$, the GAN including a generator producing a synthetic image and a discriminator trained to discriminate between real images and synthetic images. The generator and discriminator are trained to minimize a plurality of loss components so as to improve the realism of the synthetic images produced by the generator, as discussed in detail below.

The methodology then includes a final step of supplying a semantic map (e.g., defining a particular pathology, and skin color) to the trained GAN and responsively generating the synthetic image. This synthetic image shows the particular pathology and skin color as specified in the semantic map.

In one possible example, the method can be performed iteratively by generating a series of synthetic images wherein during the repeated iterations the component of the semantic map encoding skin color is varied. For example, in this manner a given pathology can be reproduced but the skin color in the image is progressively darkened so as to span the full spectrum of human skin color variation. As another example, one can do repeated iterations of generating synthetic images and the component of the semantic map encoding pathology is varied while maintaining the component of the semantic map encoding skin color constant. This will produce a variety of skin pathologies (including rare or unrepresented pathologies in the dataset) in a given skin color. One could of course vary both the skin color, size, and/or pathology semantic components in an iterative generation of synthetic images with varying skin color, pathology size and pathology type.

As noted above, the synthetic images created in accordance with this method can be used to augment a training set used for developing a skin condition classifier, and improve the performance of the classifier, e.g., its ability to correctly classify rare skin conditions or skin conditions that are poorly represented in a training set.

In this aspect, a method for training a skin condition classifier includes steps of obtaining a heterogeneous dataset, in the form of a multitude of ground truth annotated clinical skin images presenting a variety of pathologies and obtained from a multitude of patients with varying degrees of skin color, to improve the signal to noise ratio. In one example the clinical skin images are generated with consumer grade cameras. This heterogeneous dataset is a training set for training a machine learning classifier, and in this method the previously described step of preprocessing the heterogeneous dataset is optional and not required.

The method includes the step of adding to the training set a multitude of synthetic images generated from a trained generative adversarial network (GAN) to as to increase the number of images in the training set reflective of rare skin conditions and/or remove bias present in the dataset, thereby producing an augmented training set.

The method then includes a step of training a deep convolutional neural network to classify skin conditions from the augmented training set.

As noted above, one possible clinical use of the synthetic images is augmenting an image database with the synthetic image, so as to make the images available for search and retrieval. The image database could be made available for training clinicians, e.g., nurse practitioners or general practitioners, in advanced training of dermatologist, or education and informal self-diagnosis by the general population.

DETAILED DESCRIPTION

Figure 1:
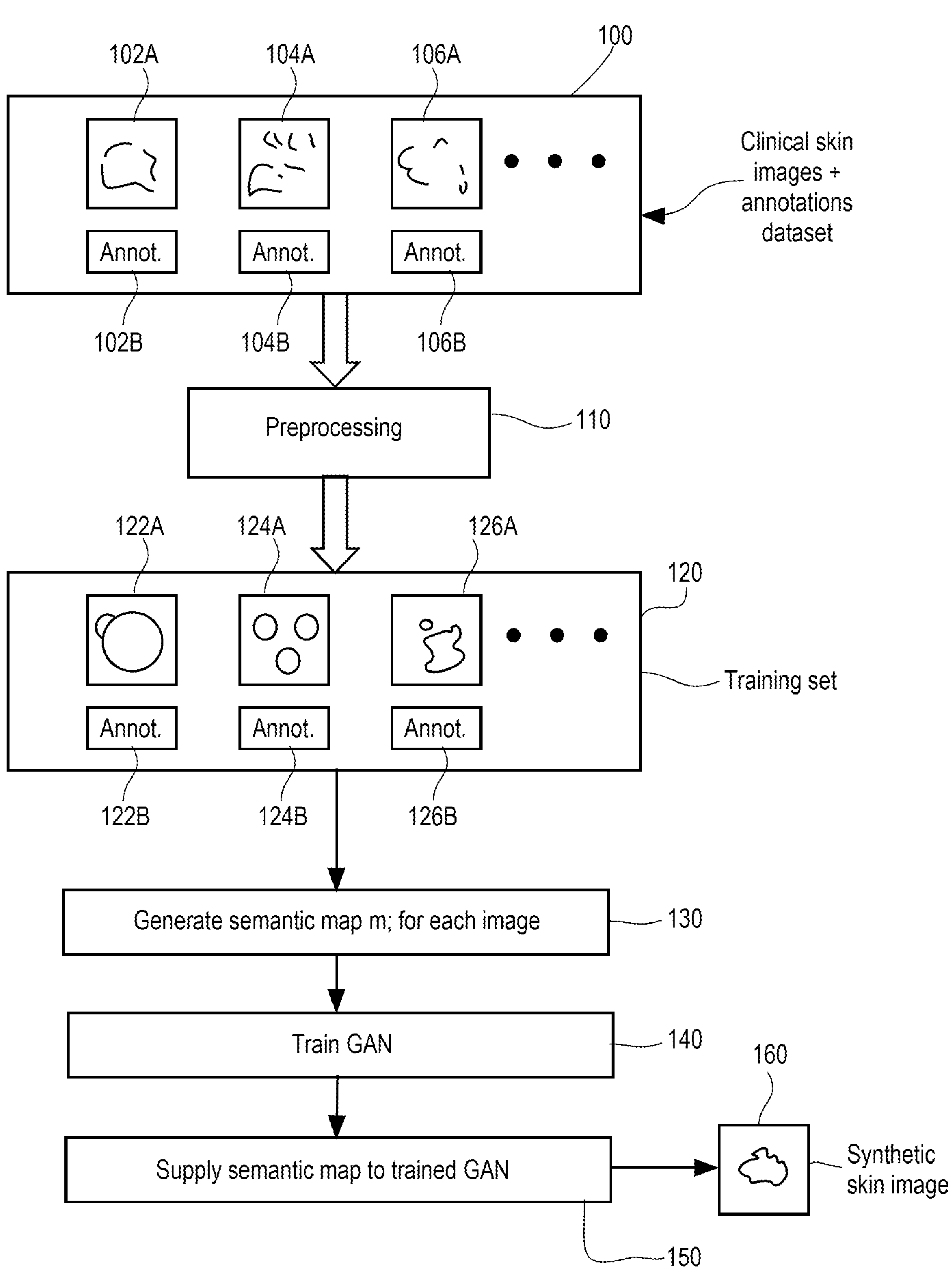
FIG. 1 is a flow chart showing a method of training a GAN and generating a synthetic skin image.

FIG. 1 is an overview of our method of generating synthetic skin images with pathology. The method makes use of a heterogeneous dataset 100 in the form of a multitude of ground truth annotated clinical skin images 102A, 104A, 106A, etc. presenting a variety of pathologies and obtained from a multitude of patients with varying degrees of skin color. Each image is associated with an annotation 102B, 104B, 106B etc., which identifies the associated pathology or condition in the image. An example of the dataset 100 is given in detail below. The images 102A, 104A etc. were annotated with ground truth by board certified dermatologists to differentiate among 26 common skin conditions and an additional 'other' category. The images 102A, 104A, etc. in the dataset include extraneous features including hair, clothing, etc. and the background is unique to each individual and non-uniform across the dataset. To improve the signal to noise ratio, a preprocessing step 110 is performed on the dataset: creating one or more region of interest (ROI) bounding boxes for each image such that the pathology present in the clinical skin images is prominent within such bounding boxes, thereby creating a more uniform version of the data set. This more uniform version is referred to as the "training set" below, and shown in FIG. 1 as 120. The images 122A, 122A etc. in FIG. 1 are the cropped regions of the original image with the pathology and the annotations 102B, 104B etc., are carried forward and present and associated with each cropped image as shown at 122B, 124B etc.

The methodology further includes a step of, for each (cropped) image in the training set created as described above, generating a corresponding semantic map in that encodes the skin color, pathology, size and location of the pathology within the image (ROI), thereby generating input pairs $\{x_i; m_i\}$ where $x_i$ is an image in the training set 120, and i=1 . . . N, wherein N is the number of cropped images in the training set. It will be noted that there may be more than one cropped image for each image 102A, 104A . . . in the dataset 100; the main thing is that training set includes a very large number of cropped image/annotation pairs, typically many thousands of such pairs.

The methodology then includes a step 140 of training a generative adversarial network (GAN) (see FIG. 4 and the following discussion) with the input pairs $\{x_i: m_i\}$, the GAN including a generator 202 (FIG. 4) producing a synthetic image and a discriminator 204 (FIG. 4) trained to discriminate between real images and synthetic images. The generator and discriminator are trained to minimize a plurality of loss components so as to improve the realism of the synthetic images produced by the generator, discussed in detail below.

The methodology then includes a final step 150 of supplying a semantic map (e.g., defining a particular pathology, and skin color, and size) to the trained GAN and responsively generating the synthetic image 160 as specified in the semantic map. This synthetic image shows the particular pathology and skin color, per the semantic map. This last step can be repeated in many iterations while changing one or more of the parameters of the semantic map and holding the others constant, e.g., to generate a series of synthetic images of a given pathology with different shades of underlying skin color.

With the above discussion in mind, the following discussion will explain the dataset 100 (FIG. 1), preprocessing step, and GAN model (FIG. 4) training and use in more detail.

Dataset 100 and Preprocessing Step 110

For the work described in this document, we used a dataset provided by a tele-dermatology service, collected in 17 clinical sites in two U.S. states from 2010 to 2018. This dataset consisted of 9,897 cases and 49,920 images; each case contains one or more high resolution (resolution range: 600×800 to 960×1280) images obtained from consumer grade cameras. Ground truth of the skin condition was established for each case by an aggregated opinion of several board-certified dermatologists to differentiate among 26 common skin conditions and an additional 'other' category. It is important to note that even though the 26 skin conditions are known to be highly prevalent, the dataset itself was unbalanced, especially for certain malignant conditions like Melanoma, which had less than 200 examples. More details on the original dataset can be found in Y. Liu, et al., *A deep learning system for differential diagnosis of skin diseases*, arXiv preprint arXiv:1909.05382 (2019).

In addition to the skin condition, we make use of two additional pieces of information: 1) for each condition, its presence in the image is marked by a Region of Interest (ROI) bounding box (FIGS. 1(*b*)) and 2) the skin color given for each case based on the Fitzpatrick skin color scale that ranges from Type I ("pale white, always burns, never tans") to Type VI ("darkest brown, never burns"). Both the ROI and the skin color annotations are determined by the aggregated opinions of several dermatologist-trained annotators.

Figure 2:
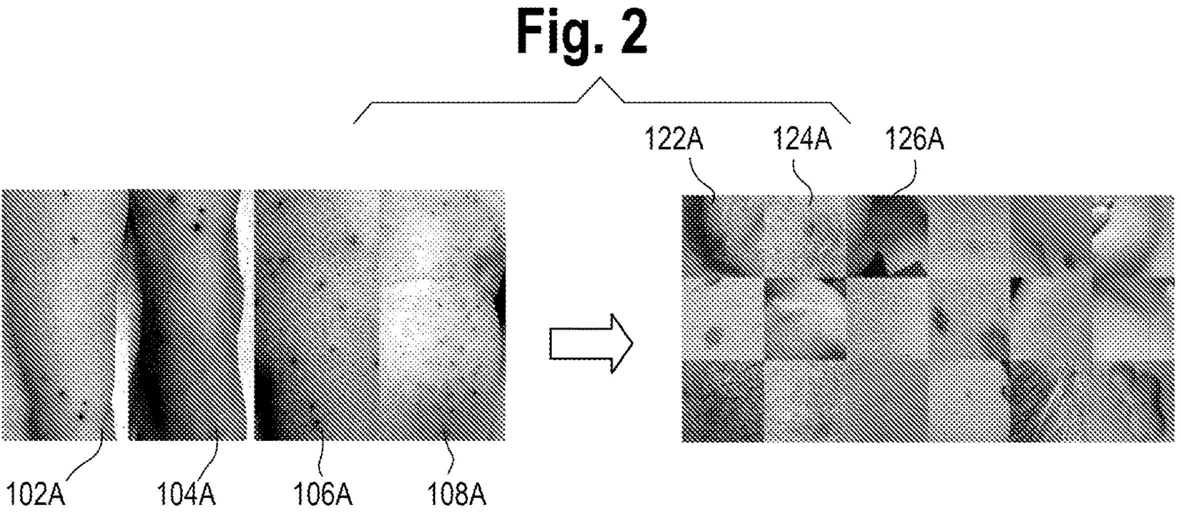
FIG. 2 illustrates one example of several original, uncropped images from a clinical dataset on the left, with varying size, scale and quality, and the result of pre-processing step on the right in which the images are cropped to smaller ROIs so as to increase the signal to noise ratio.
Figure 3:
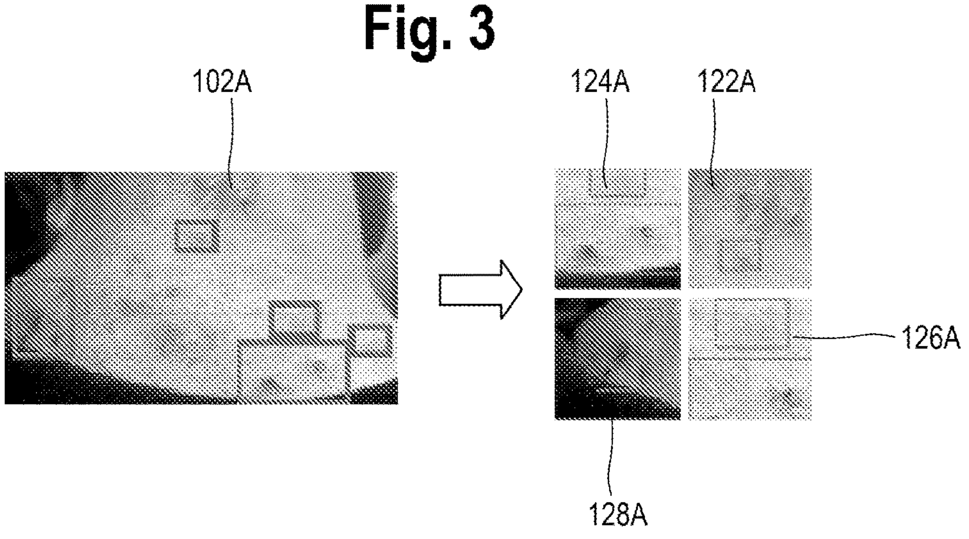
FIG. 3 illustrates another example of an original, uncropped clinical image taken with a consumer grade camera on the left and cropped images on the right with clear skin condition in focus.

The left hand side of FIGS. 2 and 3 shows the heterogeneous nature of this dataset. As stated previously, the region occupied by the skin condition varies significantly and the backgrounds are non-uniform and unique to each individual image (walls, hospitals, clothing, etc.). As a result, the signal to noise ratio is very low in most of the images. To alleviate this problem, using the annotated ROI bounding boxes, in the preprocessing step 102 we create a more uniform version of the dataset where the skin conditions is prominent in each mage. We devise a simple heuristic that crops a random window around an ROI or a group of adjacent ROIs while removing the presence of background information. This results in 40,000 images of size 256×256 for training the generative models and 24,000 images for evaluation. Examples of the cropped, ROI images forming the training set for the GAN model are shown in the right hand side of FIGS. 2 and 3.

Problem Formulation and Generation of Semantic Maps m

Given a set of input-output pairs $\{(x_i, m_i)\}^N_{i=1}$, for each real image (212, FIG. 4) $x_i \in R^{W \times H \times C}$, $m_i \in R^{W \times H}$ is its corresponding semantic map (210, FIG. 4) that encodes the skin color, the skin condition present in the image 212, its size and the location of the condition in the image. For a fully defined semantic map m, due to the possible variations (amount of hair on the skin, shooting angles, lighting conditions, morphology of the condition, etc.), the corresponding image x is not unique. The variations can be modeled by a conditional probability distribution P (x|m). Our goal is to be able to sample from P (x|m) for arbitrary and valid m. This image to image translation problem can be addressed using the conditional GAN framework (see M. Mirza et al., Conditional generative adversarial nets. arXiv preprint arXiv:1411.1784 (2014)) which has been successfully used in similar settings. See e.g., P. Isola, J.-Y. Zhu et al. Image-to-image translation with conditional adversarial networks. Proceedings of the IEEE conference on computer vision and pattern recognition, pages 1125-1134 (2017); T.-C. Wang, et al., High-resolution image synthesis and semantic manipulation with conditional Bans, Proceedings of the IEEE conference on computer vision and pattern recognition, pages 8798-8807 (2018).

Figure 4:
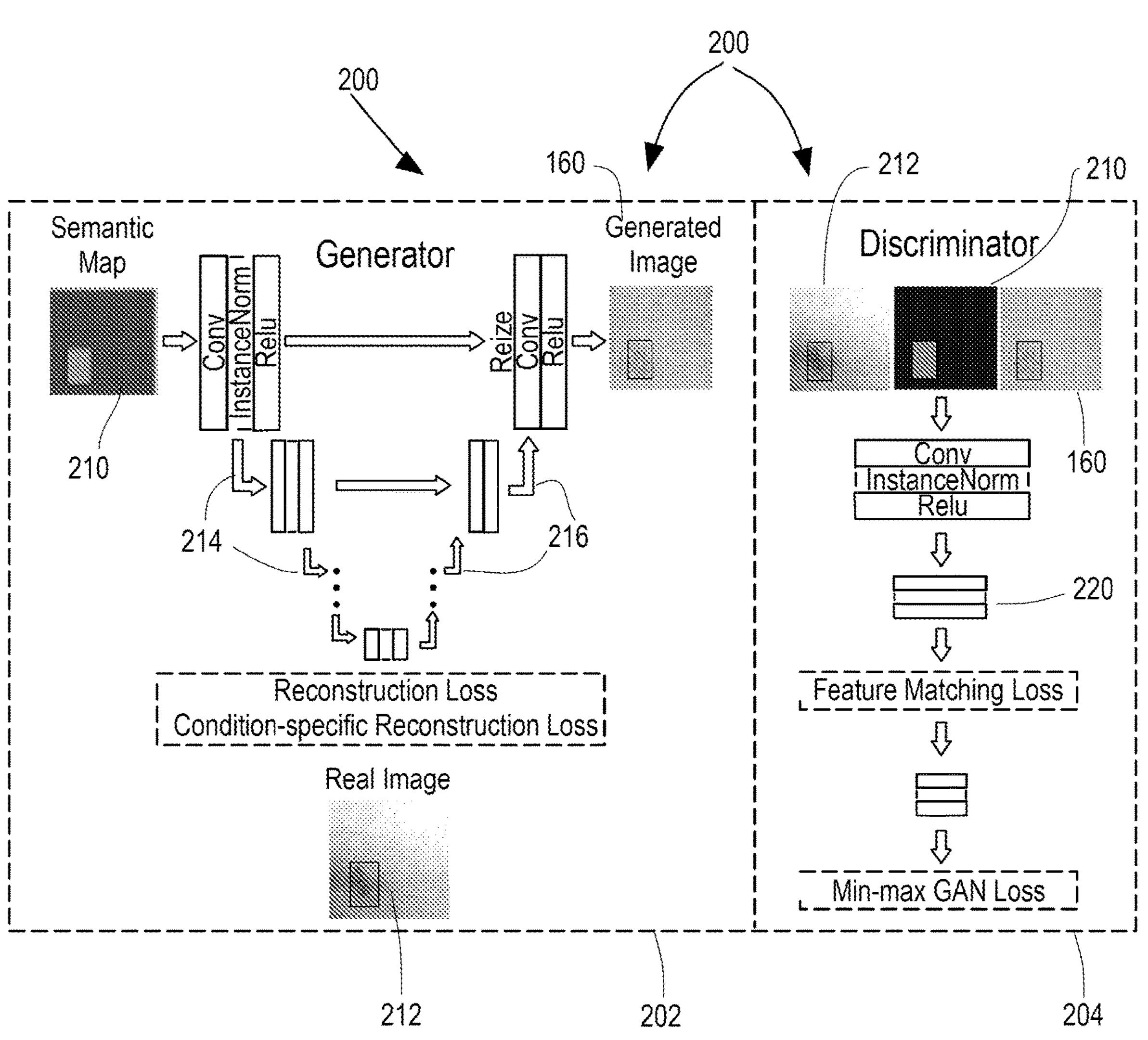
FIG. 4 is an illustration of a GAN model architecture which generates synthetic skin images. The architecture includes a Generator and a Discriminator. A semantic map encoding the skin condition, size, region of presence and the skin color is passed through the Generator to produce a synthetic image. The Generator is a modified U-Net (see O. Ronneberger, et al., *U-net: Convolutional networks for biomedical image segmentation*. International Conference on Medical image computing and computer-assisted intervention, pages 234-241. Springer, (2015), the content of which is incorporated by reference herein), where the deconvolution layers are replaced with a resizing layer followed by a convolution to mitigate the checkerboard effect. The Discriminator has a fully-convolutional architecture. The two architectures are trained to minimize four loss components: reconstruction loss for the whole image, reconstruction loss for the region of the condition, feature matching loss for the second to last activation layer of the Discriminator, and the min-max GAN loss.

For each image in our dataset, the semantic map 210 is an RGB image. The R-channel encodes the skin color and the condition is encoded in the G & B channels by a non-zero value corresponding to its ROI bounding box(es). An example is shown in FIG. 4 at 210. Given the pairs of preprocessed skin images and their semantic maps, the problem of synthetic image generation reduces to mapping any arbitrary semantic map to a corresponding skin condition image.

DermaGAN Model Architecture (FIG. 4)

The Pix2Pix model (see the Isola et al. article cited previously) gives a two-fold solution to this problem: An encoder-decoder architecture such as U-Net (see the Ronneberger et al. article cited previously) is trained with an $L_1$ reconstruction loss to reproduce a given real image from its semantic map. This is the Generator 202 of FIG. 4, which is trained to produce a generated synthetic image 160. The main drawback, however, is that such a model produces blurry images 160 that lack the details of a realistic image. Therefore, a second model (Discriminator 204 of FIG. 4), in the form of a fully convolutional neural network with layers 220 is added to discriminate real images (212) from synthetic ones (160) by looking at them on a patch level. The addition of this min-max GAN loss results in generation of realistic images with fine-grained details. Subsequent work by others improved the Pix2Pix method by applying various adaptations to the original algorithm: using several discriminator networks with various patch-sizes, progressively growing the size of generated images, using conditional normalization layers instead of instance normalization layers, and so forth. See e.g., T. Park, et al., *Semantic image synthesis with spatially adaptive normalization*, Proceedings of the IEEE Conference on Computer Vision and Pattern Recognition, pages 2337-2346 (2019); Y. Choi et al., Stargan: *Unified generative adversarial networks for multi-domain image-to-image translation*. Proceedings of the IEEE Conference on Computer Vision and Pattern Recognition, pages 8789-8797 (2018). Similarly, in our work, based on the specifics of our data modality we apply three main adaptations to the original Pix2Pix algorithm:

1. Checkerboard Effect Reduction

The original Pix2Pix generator implementation makes use of transposed convolution layers. Using deconvolution layers for image generation can results in "checkerboard" effect. The problem was resolved by replacing each deconvolution layer with a nearest-neighbor resizing layer followed by a convolution layer. These layers are shown in the Generator at 214 and 216.

2. Condition-Specific Loss

The original Pix2Pix loss function uses the L1 distance between the original 212 and synthetic image 160 as a loss function component. For skin condition images, a generator model's reconstruction performance is more important in the condition ROI compared to its surrounding skin. Therefore, we add a condition-specific reconstruction term which is simply the L1 distance between the condition ROIs in the synthetic and real images 160 and 212.

3. Feature Matching Loss

Feature matching loss enforces the generated images to follow the statistics of the real data through matching the features of generated and real images in a chosen layer(s) of the discriminator. It is computed as the L2 distance between the activations of synthetic images in a chosen discriminator layer (or layers) and that of the real images. Apart from improving the quality of generated images, feature matching loss results in a more stable training trajectory. We used the output of the discriminator's second last convolutional layer to compute the feature matching loss.

All in all, the resulting model has four loss terms: reconstruction loss, condition-specific reconstruction loss, min-max GAN loss, and feature-matching loss. Grid-search hyperparameter selection was performed to choose the weighting coefficients for each loss component. During model training, these loss terms are all minimized in order to improve the realism of the generated images 162.

EXAMPLES

Figure 5:
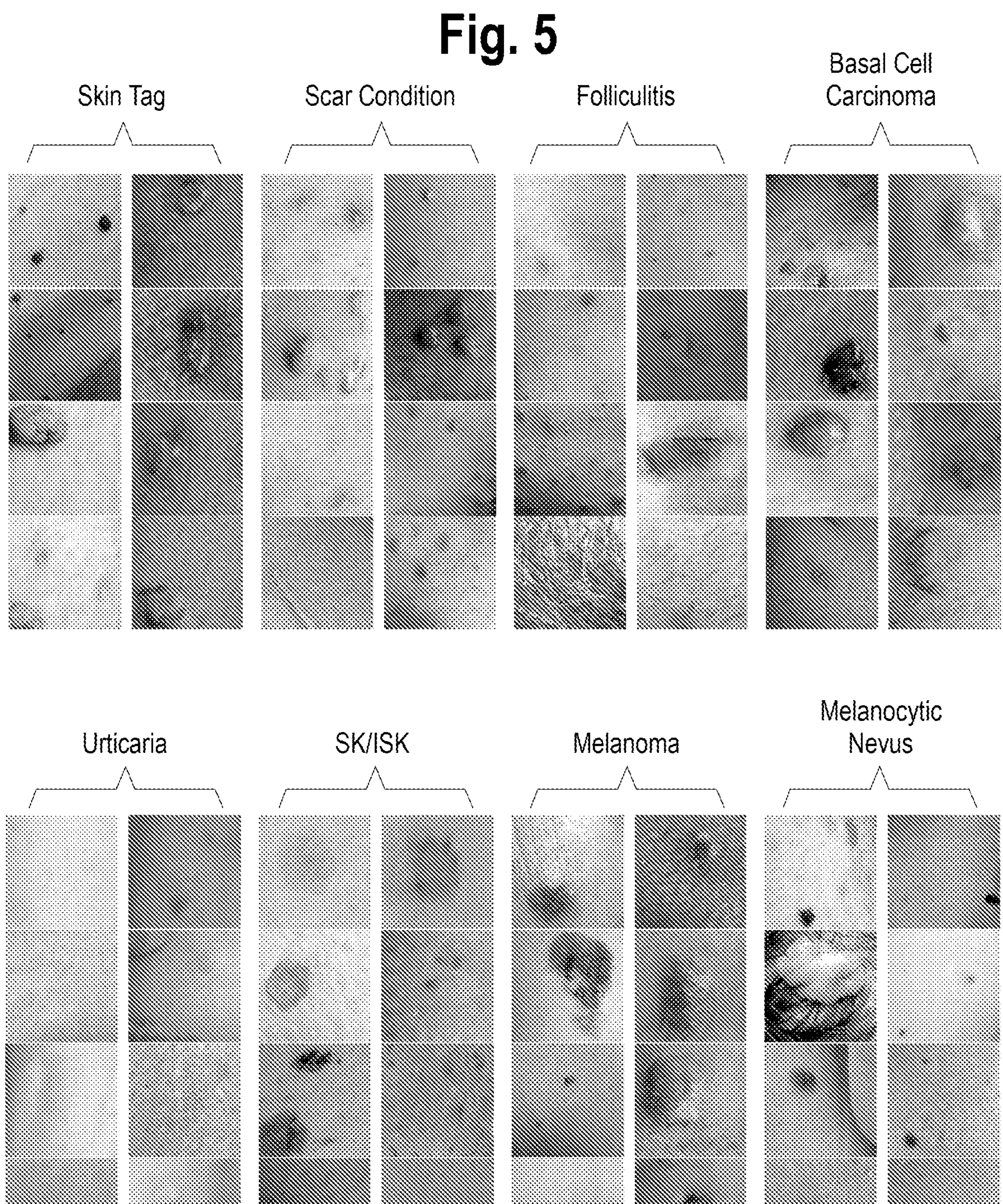
FIG. 5 shows comparisons between real images and synthetic images generated from the architecture of FIG. 4 for eight different skin conditions; for each condition the real image is shown in the left-hand column and the synthetic image is shown in the right hand column.

Using the pre-processed dataset ("training set" 110 of FIG. 1), we trained a DermGAN model (FIG. 4, as explained above) to generate synthetic skin images with a chosen skin color, skin condition, as well as the size and region of the condition. In order to focus more on the critical and rare conditions, of the 26 classes in the original data, we choose 8 conditions that have fewer samples compared to other classes (17% of the dataset combined). Examples of our generated images are shown in FIG. 5. For each condition, the left hand column shows samples of real images and the right hand column shows samples of generated synthetic images.

Synthetic Images with Different Skin Colors

Figure 6:
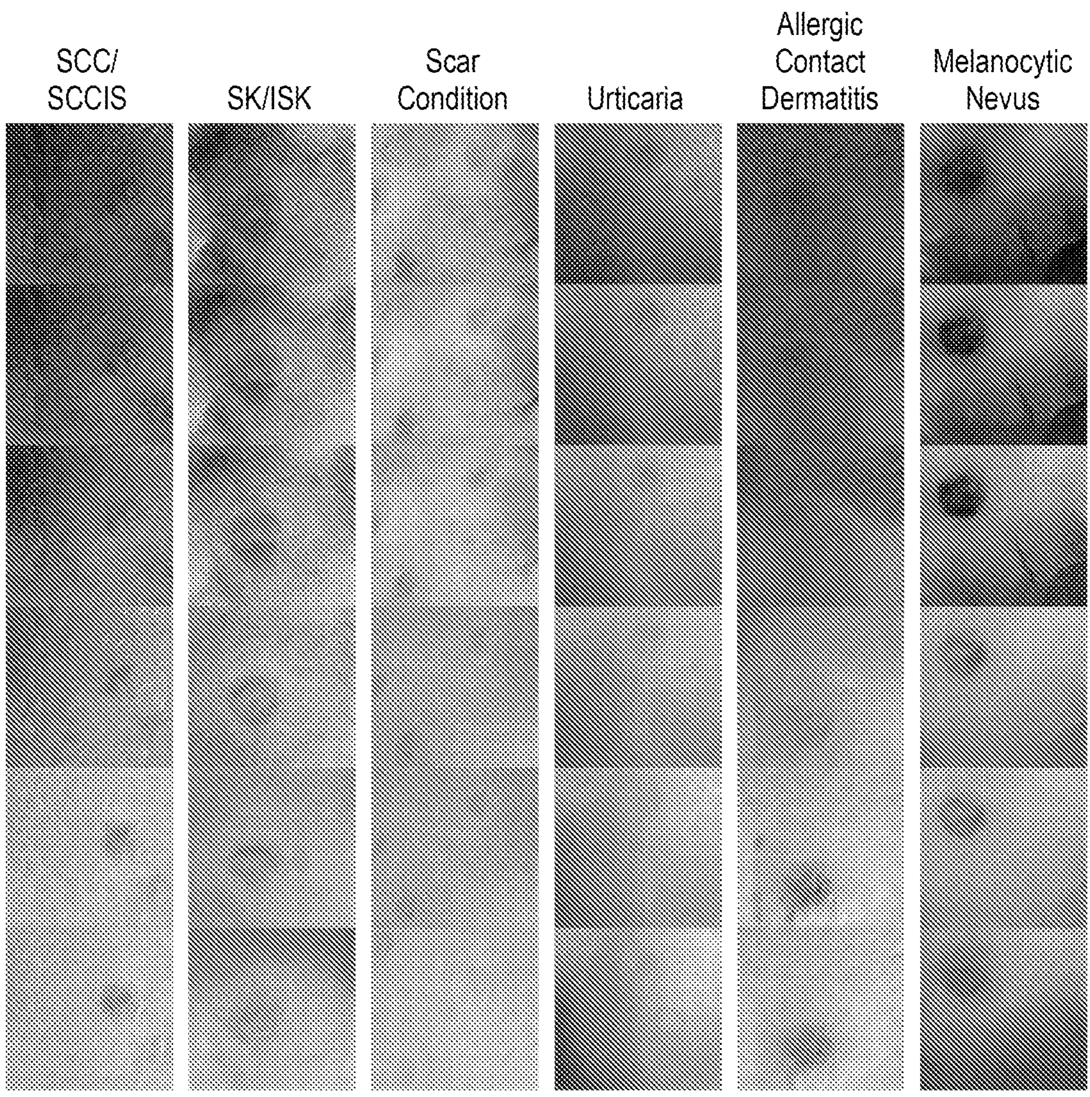
FIG. 6 shows examples of synthetic images of six different skin conditions with the underlying skin color varied in six different degrees for each condition.

In this and the subsequent experiment below, we trained a DermGAN model on all of the 26 conditions of the dataset to represent synthetic images reflective of wider demographics than were present in the original dataset. For a given semantic map in the test set, we vary the encoded background color parameter in the semantic map and observe the respective changes in the generated image. FIG. 6 depicts examples of this experiment, in which the encoded skin color of a semantic map is replaced with each of the six types. As illustrated in the figure, the DermGAN model is able to change the background skin color while adjusting the condition itself to reflect this change. For instance, for Melanocytic Nevus, the generated image for the darker tone has also a darker mole, which mimics real data.

Synthetic Images with Different Sizes of Skin Colors

Figure 7:
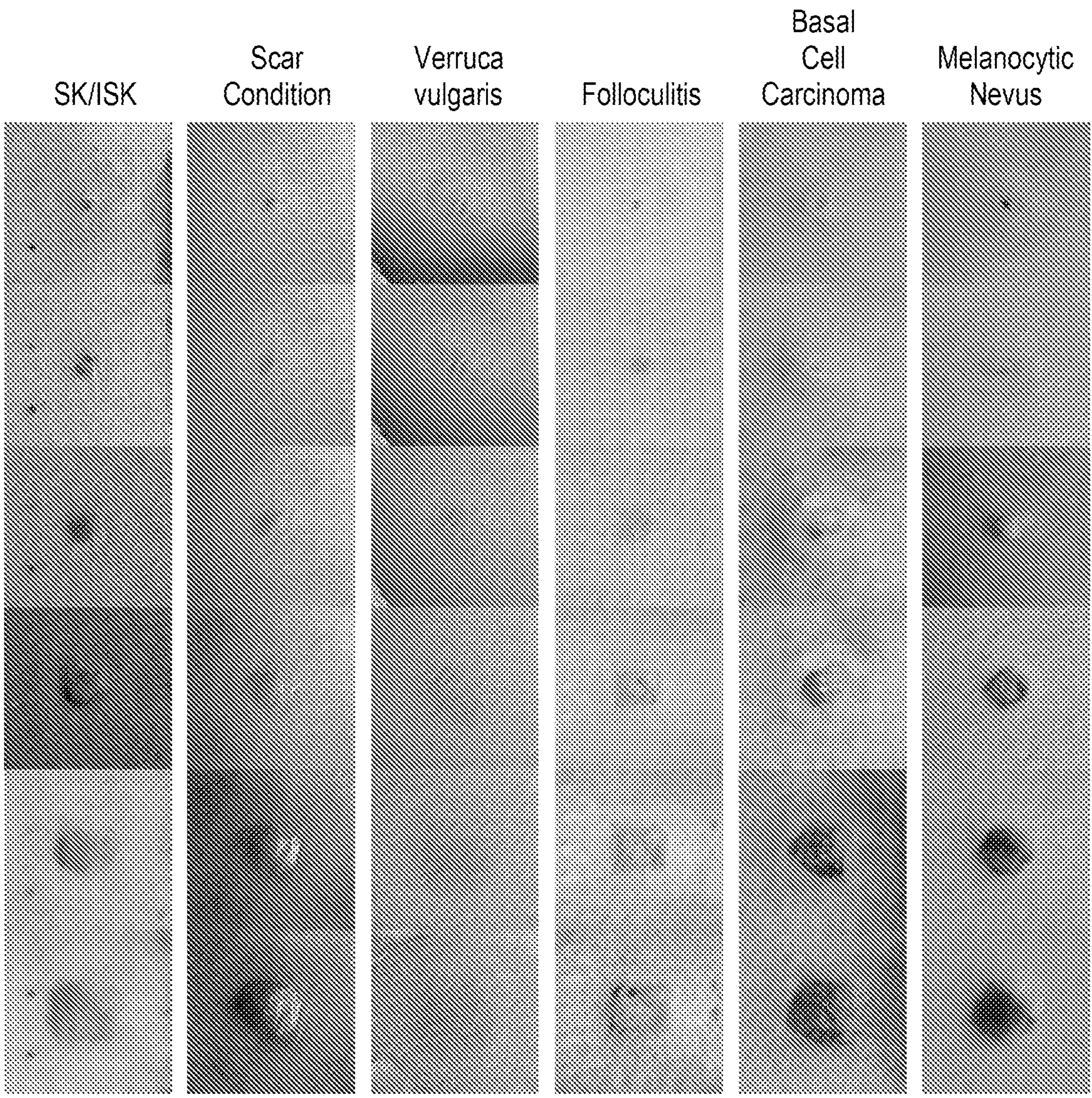
FIG. 7 shows examples of synthetic images of six different skin conditions with the size of the pathology in each condition varied in six different sizes.

For a given semantic map, we can vary the sizes of the pathological region for each skin condition and observe the respective changes in the generated image. FIG. 7 shows examples of this experiment, in which the size of the bounding box of a semantic map is gradually increased. We observe that as the size of the skin condition changes, the visual appearance also changes, which is consistent with real world occurrences.

GAN Evaluation Metrics

A perfect objective evaluation of GAN-generated images remains a challenge. One widely-used measure is the inception score that works as a surrogate measure of the diversity and the amount of distinct information in the synthetic images. It is computed as the average KL-divergence between the class probabilities assigned to a synthetic sample by an Inception-V3 model trained on the ImageNet dataset and the average class probabilities of all synthetic samples. The main drawback that makes the use of inception score inadmissible in our case is that it assumes the classes in the data set at hand to be a subset of the 1000 ImageNet classes. Another widely-used measure is the Frechet Inception Distance (FID). FID directly measures the difference between the distribution of generated and real images in the activation space of the "Pool 3" layer of the Inception-V3 model. We perform an ablation study of the DermGAN model. Results on our test set (24,000 images) are reflected in Table 1 (confidence intervals are for 50 trials).

Figure 10A:
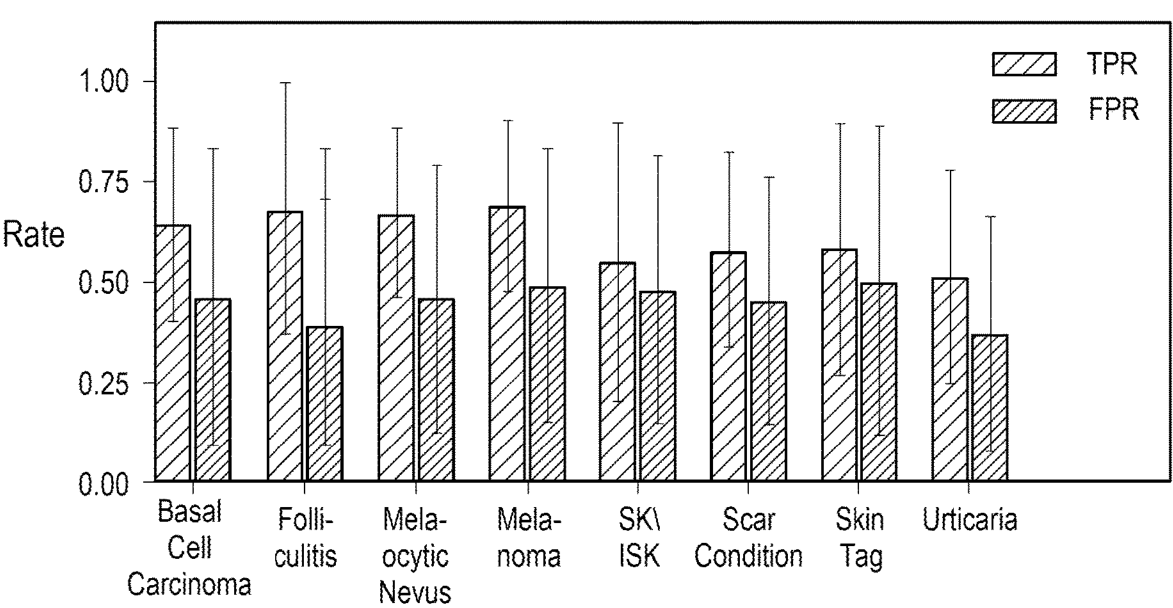
FIGS. 10A and 10B are plots showing the results of a Human Turing test on real images and synthetic images generated from the GAN model of this disclosure; results for discriminating between real and synthetic images are shown in FIG. 10A, whereas results for whether images correctly describe the respective skin condition are shown in FIG. 10B. Error bars represent standard deviation.
Figure 10B:
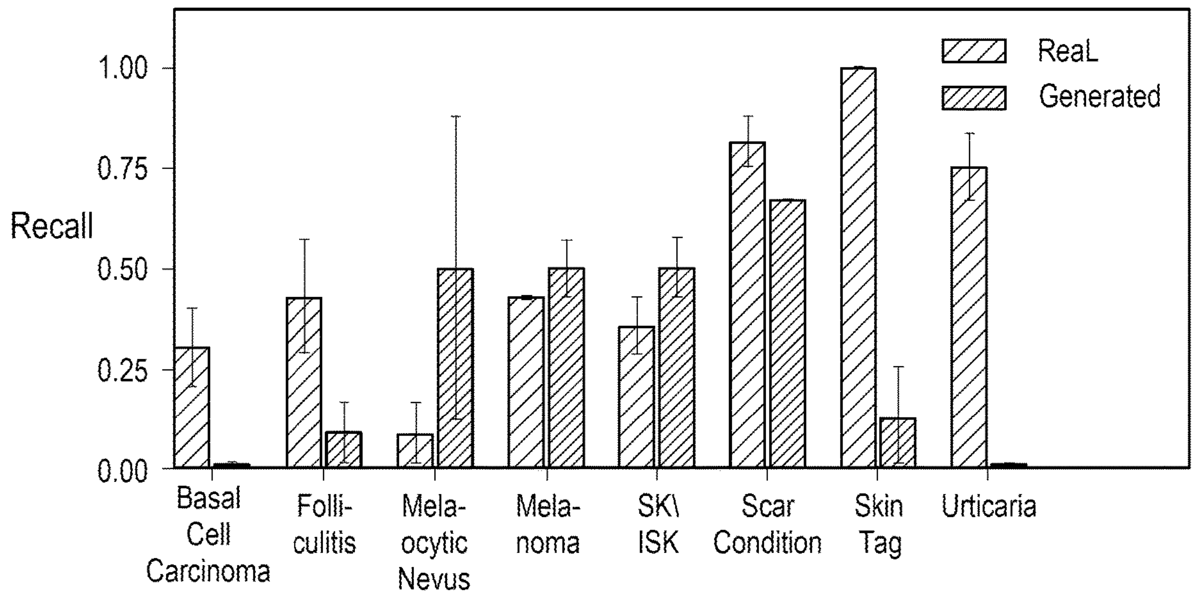

FIG. 10(*b*), with recall ranging from 0.3 to 1.00 for real images and from 0.00 to 0.67 for synthetic images. For Melanocytic nevus, Melanoma, and Seborrheic Keratosis/Irritated Seborrheic Keratosis (SK/ISK), synthetic images were identified to better represent the respective skin condition, indicating that our approach is able to preserve the clinical characteristics of those skin conditions.

Synthetic Images as Data Augmentation for Training a Skin Condition Classifier

We first trained a MobileNet model (see A. G. Howard et al., *Efficient convolutional neural networks for mobile vision applications* arXiv preprint arXiv:1704.04861 (2017)) on our original (uncropped) data to differentiate between 27 skin condition classes (26 plus "other") from a single image. This baseline model achieves a top-1 accuracy of 0.496 on a test set of 5206 images, with poor performance on some of the rare conditions. To help alleviate this issue, we generated 20,000 synthetic images using the 8-class DermGAN model (FIG. 4) and added them to the existing training data. We trained another MobileNet skin condition classifier using this augmented dataset and evaluated its performance on the same test set. While the top-1 accuracy remains relatively unchanged (p=0.56 using paired T-test), performance improves for some of the malignant relatively rare classes: Melanoma F1 score increases from 0.148 ([0.067, 0.193], 95% confidence interval using bootstrapping) to 0.282 ([0.110, 0.356]), whereas Basal cell carcinoma F1 score increases from 0.428 ([0.343, 0.439]) to 0.458 ([0.301, 0.534]), though at the cost of misclassifying Melanocytic nevus (0.113 decrease in F1). For the other 5 classes, the performances between the two models are comparable. Conventional data augmentation techniques (flipping, saturation, jitters) were used in both of the training setups.

TABLE 1

Ablation study of GAN evaluation FID score

| | Real Data | Derm GAN | No checker-board effect mitigation | No condition-specific reconstruction loss | No feature matching loss |
|---|---|---|---|---|---|
| FID (±1.96 STD) | 83.6 ± 2.5 | 122.4 ± 3.4 | 151.6 ± 3.4 | 174.0 ± 4.7 | 140.7 ± 2.5 |

Human Turing Test

For a subjective measure of how realistic the generated images are, we conducted two qualitative experiments. The first test was a Turing test with 10 participants. Each participant was asked to choose the skin images they found realistic in a collection of 80 real and 80 randomly selected synthetic images. On average the true positive rate (TPR) (the ratio of real images correctly selected) is 0.52 and the false positive rate (FPR) (the ratio of synthetic images detected as real) is 0.30. Results for each condition are demonstrated in FIG. 10(*a*), with average TPR ranging from 0.51 to 0.69 and average FPR from 0.37 to 0.50. As expected, the TPR is higher than FPR for all conditions. However, the high FPR rate among all conditions indicates the high fidelity of synthetic images.

Figure 8:
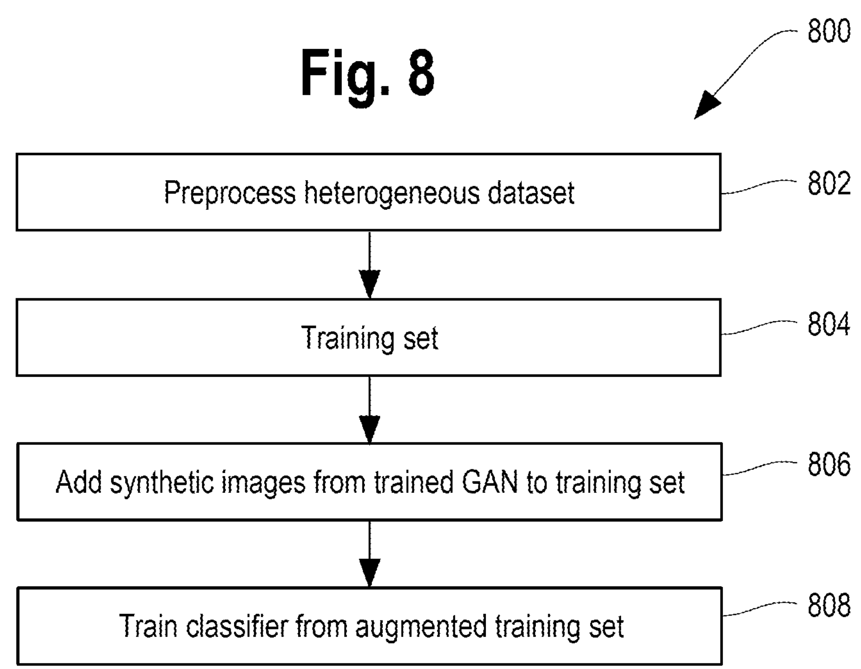
FIG. 8 is a flow chart showing a method of training a classifier using a training set of images augmented with synthetic images in order to reduce bias and improve the ability of the classifier to classify rare conditions.

The second experiment was designed to measure the medical relevance of the synthetic images. In this experiment, two board certified dermatologists answered a set of 16 questions. In each question, the participants were asked to choose the images relevant to a given skin condition among a combined set of real and randomly selected synthetic images. The average recall (ratio of related images correctly chosen) is 0.61 and 0.45 for the real and synthetic images respectively. Results for each condition are shown in In summary, the synthetic images created in accordance with this method can be used to augment a training set used for developing a skin condition classifier, and improve the performance of the classifier, e.g., its ability to correctly classify rare skin conditions or skin conditions that are poorly represented in a training set. In particular, as shown in FIG. 8, a method 800 for training a skin condition classifier includes a step 802 of obtaining a heterogeneous dataset, in the form of a multitude ground truth annotated clinical skin images (see FIG. 1, 100) presenting a variety of pathologies and obtained from a multitude of patients with varying degrees of skin color. In one example the clinical skin images are generated with consumer grade cameras. In this example, the heterogeneous dataset is a training set for training a classifier, and the preprocessing step on the heterogeneous dataset described previously is not required. The method includes a step 806 of adding to the training set a multitude of synthetic images generated from a trained generative adversarial network (GAN) to as to increase the number of images in the training set reflective of rare skin conditions and/or remove bias present in the dataset, thereby producing an augmented training set. The method continues with a step 808 of training a classifier, such as a deep convolutional neural network, to classify skin conditions from the augmented training set.

As noted above, one possible clinical use of the synthetic images is augmenting an searchable image database with the synthetic image(s), so as to make the images available for search and retrieval. The image database could be made available for training clinicians, e.g., nurse practitioners or general practitioners, in advanced training of dermatologist, or education and informal self-diagnosis by the general population.

Figure 9:
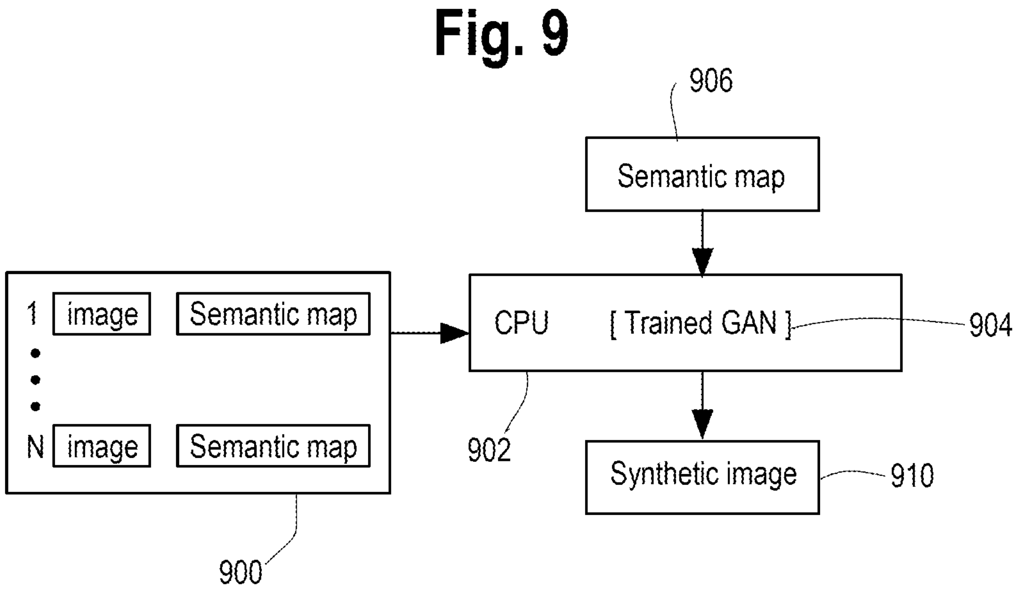
FIG. 9 is a block diagram of a system configured for generating synthetic skin images.

In yet another aspect, it will be appreciated that we have disclosed an apparatus configured for generating a synthetic clinical skin image with pathology. In particular, referring to FIG. 9, a memory 900 stores a multitude (N) of input pairs $\{x_i; m_i\}$, in the form of images $x_i$ and a corresponding semantic map $m_i$ that encodes the skin color, pathology and location of the pathology within the image $x_i$ and i=1 . . . N. A processing unit 902 (e.g., general purpose computer) executes a generative adversarial network (GAN) 904 trained from the input pairs. The GAN including a generator (FIG. 4, 202) producing a synthetic image and a discriminator (FIG. 4, 204) trained to discriminate between real images and synthetic images, wherein the generator and discriminator are trained to minimize a plurality of loss components so as to improve the realism of the synthetic images. The processing unit is configured to generate a synthetic clinical skin image with pathology from an input comprising a semantic map 906.

In one embodiment, the semantic map is defined so as to specify a pathology type, pathology size, or skin color. The loss components minimized in training of the GAN include reconstruction loss, lesion-specific reconstruction loss, min-max GAN loss, and feature matching loss. In one configuration, the generator is configured with a nearest-neighbor resizing layer followed by a convolution layer to thereby reduce a checkerboard effect in generated images.

CONCLUSION

We have described a method for generating synthetic clinical images with skin conditions as seen in a teledermatology setting. We frame the problem as an image to image translation task and propose DermGAN (FIG. 4), an adaptation of the popular Pix2Pix GAN architecture. Using the proposed framework we are able to generate realistic images for pre-specified skin conditions. We demonstrate that when varying the skin color or the size and location of the condition, the synthetic images can reflect such changes, while maintaining the characteristics of the respective skin condition. We further demonstrate that our generated images are of high fidelity using objective GAN evaluation metrics and qualitative tests. When using the synthetic images as data augmentation for training a skin condition classifier, the model is comparable to baseline while demonstrating improved performance on rare skin conditions.

We claim:

1. A method of generation of synthetic clinical skin images with pathology, comprising:

obtaining a heterogeneous dataset that includes a plurality of ground truth annotated clinical skin images, wherein the heterogeneous dataset represents a variety of pathologies and a plurality of patients with varying skin color;

preprocessing the heterogeneous dataset by creating at least one region of interest (ROI) bounding box for each clinical image in the heterogeneous data set such that pathology present in the clinical skin images is located within such bounding boxes, thereby creating a plurality of cropped images, with a given cropped image of the plurality of cropped images visually representing a skin pathology and associated with a ground truth annotation of an annotated clinical skin image of the plurality of ground truth annotated clinical skin images from which the given cropped image was extracted;

for each cropped image, generating a corresponding semantic map m that encodes the skin color, pathology type, and size and location of the pathology within the respective cropped image x, thereby generating input pairs $\{x_i; m_i\}$ where the index i varies from 1 to a number N of the cropped images in the plurality of cropped images;

training a generative adversarial network (GAN) with the input pairs $\{x_i; m_i\}$ such that the GAN can generate, from an input semantic map, an output synthetic image that depicts the skin color, pathology type, and pathology size and location of the input semantic map, wherein the GAN includes a generator that generates a synthetic image from an input semantic map, wherein the GAN additionally includes a discriminator that discriminates between synthetic images generated by the generator and real images, wherein training the GAN with the input pairs $\{x_i; m_i\}$ comprises updating the generator and discriminator of the GAN so as to reduce a plurality of loss components, thereby resulting in the generator generating realistic synthetic images, and wherein the loss components comprise lesion-specific reconstruction loss; and generating a synthetic image by supplying a semantic map to the trained GAN and responsively generating the synthetic image.

2. The method of claim 1, wherein the loss components further comprise reconstruction loss, min-max GAN loss, and feature matching loss.

3. The method of claim 1, wherein the GAN includes a generator that generates a synthetic image from an input semantic map, and wherein the generator comprises a nearest-neighbor resizing layer followed by a convolution layer, thereby reducing a checkerboard effect in synthetic images generated by the generator.

4. The method of claim 1, further comprising generating a plurality of synthetic images by applying a plurality of different semantic maps to the GAN, wherein the plurality of different semantic maps vary with respect to the component of the semantic maps encoding skin color.

5. The method of claim 4, wherein the plurality of semantic maps encode a pathology type that is rare relative to a population of pathology types represented in the heterogeneous dataset.

6. The method of claim 1, further comprising the step of generating a plurality of synthetic images by applying a plurality of different semantic maps to the GAN, wherein the plurality of different semantic maps vary with respect to the component of the semantic maps encoding skin color and are constant with respect to the component of the semantic map encoding skin color constant.

7. The method of claim 1, further comprising the step of generating a plurality of synthetic images by applying a plurality of different semantic maps to the GAN, wherein the plurality of different semantic maps vary with respect to the component of the semantic map encoding the size of the pathology and are constant with respect to the component of the semantic map encoding skin color constant.

8. The method of claim 1, wherein the clinical skin images of the dataset comprise photographic images of skin obtained with a consumer grade camera.

9. The method of claim 1, wherein the synthetic image depicts a melanoma, Lyme disease, or basal cell carcinoma pathology.

10. A method of training a skin condition classifier comprising:

obtaining a training set that includes a plurality of ground truth annotated clinical skin images, wherein the training dataset represents a variety of pathologies and a plurality of patients with varying skin color;

adding to the training set a plurality of synthetic images generated by a generative adversarial network (GAN) as to increase the number and variety of images in the training set such that at least one of a representation of rare skin conditions within the training set is increased or a bias present in the training dataset with respect to skin color is reduced, thereby producing an augmented training set;

wherein adding to the training set the plurality of synthetic images generated by the GAN comprises generating a plurality of synthetic images by applying a plurality of different semantic maps as input to the GAN, wherein the plurality of different semantic maps vary with respect to the component of the semantic maps encoding skin color; and using the augmented training set, training a skin condition classifier to classify skin conditions based on input clinical skin images.

11. The method of claim 10, further comprising applying data augmentation techniques on at least one of the training set or the augmented training set by at least one of flipping at least one of the ground truth annotated clinical skin images, varying a saturation of at least one of the ground truth annotated clinical skin images, or adding jitter to at least one of the ground truth annotated clinical skin images.

12. The method of claim 10, wherein the GAN includes a generator that generates a synthetic image from an input semantic map, wherein the GAN additionally includes a discriminator that discriminates between synthetic images generated by the generator and real images, wherein training the GAN with the input pairs $\{x_i; m_i\}$ comprises updating the generator and discriminator of the GAN so as to reduce a plurality of loss components, thereby resulting in the generator generating realistic synthetic images, and wherein the loss components comprise reconstruction loss, lesion-specific reconstruction loss, min-max GAN loss, and feature matching loss.

13. The method of claim 10, wherein the GAN includes a generator that generates a synthetic image from an input semantic map, and wherein the generator comprises a nearest-neighbor resizing layer followed by a convolution layer, thereby reducing a checkerboard effect in synthetic images generated by the generator.

14. The method of claim 10, wherein the plurality of semantic maps encode a pathology type that is rare relative to a population of pathology types represented in the heterogeneous dataset.

15. The method of claim 10, wherein adding to the training set the plurality of synthetic images generated by the GAN comprises generating a plurality of synthetic images by applying a plurality of different semantic maps to the GAN, wherein the plurality of different semantic maps vary with respect to the component of the semantic maps encoding skin color and are constant with respect to the component of the semantic map encoding skin color constant.

16. The method of claim 10, wherein adding to the training set the plurality of synthetic images generated by the GAN comprises generating a plurality of synthetic images by applying a plurality of different semantic maps to the GAN, wherein the plurality of different semantic maps vary with respect to the component of the semantic map encoding the size of the pathology and are constant with respect to the component of the semantic map encoding skin color constant.

17. The method of claim 10, wherein the clinical skin images of the training set comprise photographic images of skin obtained with a consumer grade camera.

* * * * *